(12) United States Patent
Clarke et al.

(10) Patent No.: US 10,835,543 B2
(45) Date of Patent: Nov. 17, 2020

(54) METHOD OF INCREASING MUSCLE MASS AND STRENGTH AND COMPOSITIONS THEREFOR

(71) Applicant: Sports Nutrition Research, Ltd., Franklin Square, NY (US)

(72) Inventors: Robert Clarke, Franklin Square, NY (US); Matthew Cahill, Franklin Square, NY (US); Brian Sweet, Oceanside, NY (US)

(73) Assignee: Sports Nutrition Research, LTD., Franklin Square, NY (US)

( * ) Notice: Subject to any disclaimer, the term of this patent is extended or adjusted under 35 U.S.C. 154(b) by 735 days.

(21) Appl. No.: 13/907,090

(22) Filed: May 31, 2013

(65) Prior Publication Data

US 2014/0357568 A1    Dec. 4, 2014

(51) Int. Cl.

| | |
|---|---|
| *A61K 31/661* | (2006.01) |
| *A61K 31/195* | (2006.01) |
| *A61K 38/01* | (2006.01) |
| *A61K 35/20* | (2006.01) |
| *A61K 31/685* | (2006.01) |
| *A61K 31/198* | (2006.01) |
| *A23L 33/12* | (2016.01) |
| *A23L 33/175* | (2016.01) |
| *A23L 33/19* | (2016.01) |
| *A23K 50/20* | (2016.01) |
| *A23K 20/158* | (2016.01) |
| *A23K 50/40* | (2016.01) |
| *A23K 20/147* | (2016.01) |

(52) U.S. Cl.
CPC ............ *A61K 31/661* (2013.01); *A23L 33/19* (2016.08); *A61K 31/195* (2013.01); *A61K 31/198* (2013.01); *A61K 31/685* (2013.01); *A61K 35/20* (2013.01); *A61K 38/014* (2013.01); *A61K 38/018* (2013.01); *A23K 20/147* (2016.05); *A23K 50/20* (2016.05)

(58) Field of Classification Search
CPC .... A61K 31/195; A61K 31/661; A61K 35/20; A61K 38/014; A61K 38/018
See application file for complete search history.

(56) References Cited

U.S. PATENT DOCUMENTS

| | | | | |
|---|---|---|---|---|
| 6,846,494 | B1 * | 1/2005 | Verheul-Koot et al. | 424/439 |
| 7,445,807 | B2 * | 11/2008 | Lockwood | 426/656 |
| 2005/0008678 | A1 * | 1/2005 | Howard | A23F 3/163 |
| | | | | 424/439 |
| 2011/0111066 | A1 * | 5/2011 | Ferguson et al. | 424/728 |
| 2012/0141448 | A1 * | 6/2012 | De Ferra et al. | 424/94.1 |
| 2013/0338114 | A1 * | 12/2013 | De Ferra et al. | 514/121 |

FOREIGN PATENT DOCUMENTS

| | | | | |
|---|---|---|---|---|
| WO | WO 95/20967 | * | 8/1995 | ............ A61K 31/66 |
| WO | 2008120214 | A2 | 10/2008 | |

OTHER PUBLICATIONS

Rasmussen. Phosphatidic acid: a novel mechanical mechanism for how resistance exercise activates mTORC1 signalling. J Physiol, 2009, 587, No. 14, pp. 3415-3416.*
Hoffman et al. Efficacy of phosphatidic acid ingestion on lean body mass, muscle thickness and strength gains in resistance-trained men. J Int Soc Sports Nutrition 2012, vol. 9, No. 47, pp. 1-7.*
O'Neil et al. The role of phosphoinositide 3-kinase and phosphatidic acid in the regulation of mammalian target of rapamycin following eccentric contractions. J Physiology 2009, vol. 587, No. 14, pp. 3691-3701.*
Crowe et al. Effects of dietary leucine supplementation on exercise performance. Eur J Appl Physiol. 2006, vol. 97, pp. 664-672.*
Staton. The Influence of Soya Lecithin on Muscular Strength Research Quarterly. American Association for Health, Physical Education and Recreation, 1951. vol. 22, Issue 2, pp. 201-207.*
American Lecithin Company, About Soy Phospholipids. Accessed online at http://www.americanlecithin.com/lecithin_2009 on Mar. 10, 2016, 19 pages.*
Hellhammer et al. Effects of Soy Lecithin Phosphatidic Acid and Phosphatidylserine Complex (PAS) on the Endocrine and Psychological Responses to Mental Stress. Stress, Jun. 2004. vol. 7 (s), pp. 119-126.*
About Soy Phospholipids. accessed online at http://www.americanlecithin.com/aboutphos.html on Jan. 22, 2013, pp. 1-2.*
The free dictionary. Definition of "exercise" accessed online at http://www.thefreedictionary.com/exercise on Feb. 28, 2017, pp. 1-9.*
Yong Xu et al., Activation of mTOR signaling by novel fluoromethylene phosphonate analogues of phosphatidic acid, Bioorganic & Medicinal Chemistry Letters 14 (2004) 1461-1464.
Nelo Eidy Zanchi et al., Mechanical stimuli of skeletal muscle: implications on mTOR/p70s6k and protein synthesis, Eur J Appl Physiol (2008) 102:253-263.
Nicholas Lehman et al., Phospholipase D2-derived phosphatidic acid binds to and activates ribosomal p70 S6 kinase independently of mTOR, FASEB J. 21, 1075-1087 (2007).
Troy Alan Hornberger et al., Regulation of mTOR by Mechanically Induced Signaling Events in Skeletal Muscle, Cell Cycle 5:13, 1391-1396, Jul. 1, 2006; © 2006 Landes Bioscience.
David A. Foster, Regulation of mTOR by Phosphatidic Acid?, Cancer Res 2007; 67: (1). Jan. 1, 2007.

(Continued)

*Primary Examiner* — Marcela M Cordero Garcia
(74) *Attorney, Agent, or Firm* — Kane Kessler, P.C.; Barry E. Negrin

(57) ABSTRACT

A method of increasing muscle mass and strength in mammals by orally administering a therapeutically effective amount of phosphatidic acid. The phosphatidic acid is preferably administered as a plurality of doses per day with at least one dose being administered during the anabolic window following exercise. Preferably, the method further includes the cotemporaneous administration of a therapeutically effective amount of creatine, optionally as phosphatidylcreatine. In addition or in the alternative, the method further includes the cotemporaneous administration of a therapeutically effective amount of leucine, optionally as phosphatidylleucine.

22 Claims, 1 Drawing Sheet

(56) References Cited

OTHER PUBLICATIONS

Laura S. Harrington et al., Restraining PI3K: mTOR signalling goes back to the membrane, Trends in Biochemical Sciences vol. 30 No. 1 Jan. 2005.
V Veverka et al., Structural characterization of the interaction of mTOR with phosphatidic acid and a novel class of inhibitor: compelling evidence for a central role of the FRB domain in small molecule-mediated regulation of mTOR, Oncogene (2008) 27, 585-595; doi:10.1038/sj.onc.1210693; published online Aug. 6, 2007.
T.A. Hornberger et al., The role of phospholipase D and phosphatidic acid in the mechanical activation of mTOR signaling in skeletal muscle, PNAS, Mar. 21, 2006, vol. 103, No. 12, 4741-4746.
Vandenberghe et al. "Long-term creatine intake is beneficial to muscle performance during resistance training." Journal of Applied Physiology, 1985, vol. 83, Iss. 6, pp. 2055-2064, entire document.
Zanchi et al. Mechanical stimuli of skeletal muscle: implications on mTOR/p70s6k and protein synthesis, Oct. 17, 2007 (Oct. 17, 2007), vol. 102. pp. 253-263, entire document.
Goodman et al. New roles for Smad signaling and phosphatidic acid in the regulation of skeletal muscle mass, F 1000 Prime Reports, Apr. 1, 2014 (Apr. 1, 2014), vol. 6, pp. 1-9, entire document.
International Search Report and Written Opinion of PCT/US2014/040335 dated Oct. 15, 2014.

* cited by examiner

METHOD OF INCREASING MUSCLE MASS AND STRENGTH AND COMPOSITIONS THEREFOR

BACKGROUND OF THE INVENTION

Field of the Invention

The invention relates to methods and compositions for increasing muscle mass and strength in mammals. More specifically, the invention relates to orally ingestible compositions for increasing muscle mass and strength in mammals to a greater degree than exercise alone would provide.

Description of Related Art

Maintaining one's muscles in a healthy state is critical for one's metabolism, physical performance, and overall well-being. Muscles are composed of the contractile proteins myosin and actin; together, these form myofibrils. Contraction occurs when actin ratchets over the myosin, shortening the length of the myofibrils. Like all proteins, these contractile proteins begin with a genetic response, through the ribosomal synthetic apparatus. The resulting proteins are incorporated into existing myofibrils to increase the size of the muscle, called muscular hypertrophy, or to repair the damage that occurs during contraction. This system requires adequate nutrition to provide the amino acids that form the protein. In addition, the pathways are controlled by activating factors. Muscular hypertrophy is known to be achieved by exercise, especially exercise vigorous enough to reach the anaerobic threshold. Within a short time of commencing such exercise, a mammal will achieve measurable mass increase and strength. The increased demand has caused the synthetic machinery to be up-regulated. The activating factors that may cause the up-regulation in response to demand include the second messenger system which is known to include phospholipases, protein kinases, and the like. Put another way, while it is known that exercise can increase the size and strength of mammalian muscles, other factors, such as proper nutritional intake, contribute to an increase in mammalian muscle size and strength.

There are a number of commercially available orally ingestible nutritional supplements advertised for promoting muscle growth. However, there remains a long-felt need to provide an orally ingestible nutritional supplement that can actively assist in the development and maintenance of muscular hypertrophy.

SUMMARY OF THE INVENTION

The invention is a method of increasing muscle mass and strength in mammals. The method includes the step of orally administering a composition comprising a therapeutically effective amount of phosphatidic acid. In cases where the mammal is human, the therapeutically effective amount of phosphatidic acid is expected to be 0.5-4.0 grams per day. Preferably, the therapeutically effective amount of phosphatidic acid is expected to be approximately 1.0-1.5 grams per day.

The oral administration step further includes the step of dividing the therapeutically effective amount of phosphatidic acid into a plurality of doses per day with at least one dose being administered within 1-2 hours following an exercise session. Optionally, the oral administration step is executed to an exercising subject following exercise during the anabolic window.

Optionally, the method further includes the step of orally administering 20-100 grams of protein during the anabolic window, e.g., as food. The protein may optionally be a complete protein containing all the essential amino acids, and/or it may be whey, partially hydrolyzed collagen protein, or the like.

Preferably, the method further includes the cotemporaneous administration of a therapeutically effective amount of creatine, e.g., 3-20 grams. In one embodiment, the composition includes phosphatidylcreatine.

In addition or in the alternative, the method further includes the cotemporaneous administration of a therapeutically effective amount of leucine, e.g., 2-5 grams, more preferably about 3 grams of leucine. In one embodiment, the composition includes phosphatidylleucine. Optionally, the method includes the administration of leucine, isoleucine, and valine in a 2:1:1 ratio, e.g., 4 grams leucine:2 grams isoleucine:2 grams valine.

Other variations and formulations are contemplated.

DETAILED DESCRIPTION OF THE INVENTION

Description will now be given of the invention with reference to the attached FIGS. 1-2. It should be understood that these figures are exemplary in nature and in no way serve to limit the scope of the invention, which is defined by the claims appearing hereinbelow.

The invention is a method of increasing muscle mass and strength in mammals by orally administering a therapeutically effective amount of phosphatidic acid, as well as a nutritional supplement containing a therapeutically effective amount of phosphatidic acid.

Phosphatidic acid is a known phospholipid that is a constituent of cell membranes, forming a minor portion of the total phospholipid pool in resting cells. As the smallest of the phospholipids it regularly acts as a precursor to other phospholipids, but also as a second messenger.

Figure 1:
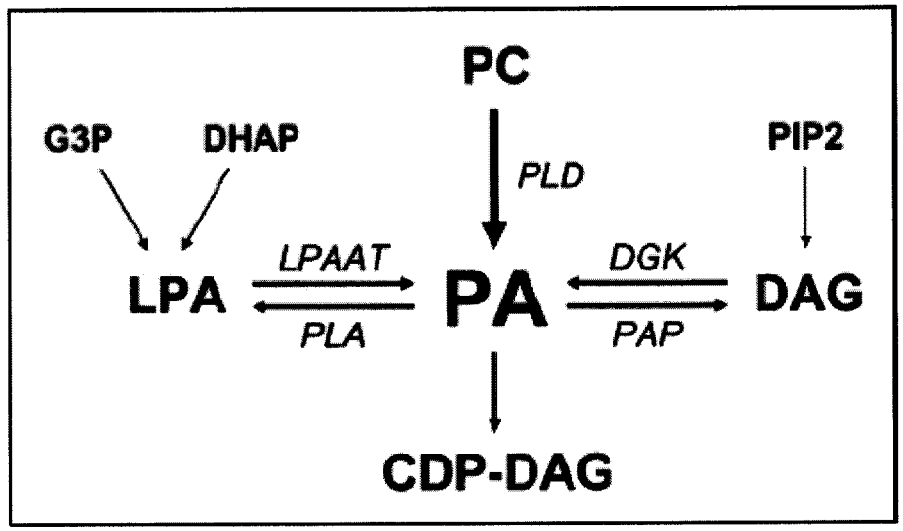
FIG. 1 is a schematic depicting various mechanisms of PA formation.
Figure 2:
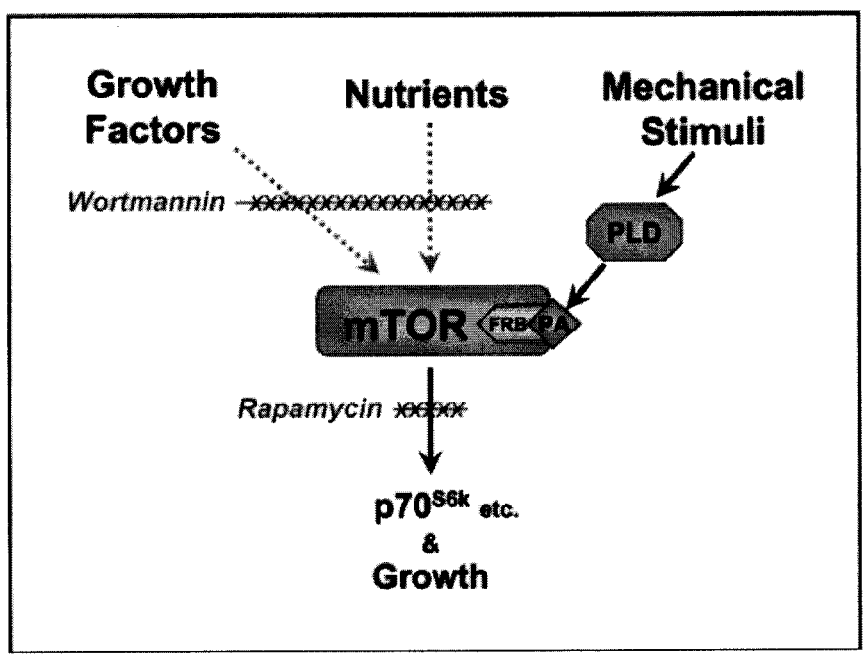
FIG. 2 is a schematic depicting PA activation.

FIG. 1 shows several possible mechanisms of PA formation, apart from brand new creation (i.e., de novo synthesis). Phosphatidic acid (PA) is primarily synthesized from phosphatidylcholine (PC) by the enzyme phospholipase D (PLD). PA can also be synthesized from lysophosphatidic acid (LPA) by the LPA acyltransferase (LPAAT). LPA is primarily derived from glycerol-3-phosphate (G3P) and dihydroxyacetone phosphate (DHAP). PA can also be synthesized from diacylglycerol (DAG) by the DAG kinase (DGK). DAG is primarily derived from phosphatidyinositol-4,5-biphosphate (PIP2). The primary enzymes responsible for PA degradation include phospholipase A (PLA), which generates LPA, and PA phosphohydrolase (PAP), which generates DAG. PA can also be degraded to cytidine diphosphate DAG (CDP-DAG) which serves as a precursor for the formation of a variety of lipids. The pathways that regulate PA concentration in response to mechanical stimulation have yet to be fully defined. (Hornberger et al, 2006.)

Under normal conditions, PA activation depends on phospholipase D (PLD) enzyme activity, which hydrolyses phosphatidilcholine to PA and choline (Hong, J H et al, 2001). PA then binds the FRB domain of a protein called mTOR and activates p70s6k activity, which is one of the key ribosomes of the translation phase of protein synthesis (Fang, Y, 2003). Another study has demonstrated that PA plays a "critical role" in the mechanical activation of mTOR signaling (T. A.

Hornberger, 2006). The study concluded several points of note. First, an elevation in PA concentration was sufficient for the activation of mTOR signaling. Second, mechanical stimulation (e.g., substantially anaerobic activity such as weight lifting) induced PLD activation, PA accumulation, and mTOR signaling. We theorize that mTOR signaling is at least partly caused by PA accumulation. Finally, if PLD is blocked, PA accumulation is also blocked, and as a consequence, mTOR signaling is prevented. Given that signaling through mTOR is necessary for mechanically-induced growth of skeletal muscle, and given that an elevation in PA is necessary for the mechanical activation of mTOR signaling, it has been theorized that mechanical stimuli induce skeletal muscle growth through a PA-dependent activation of mTOR.

This information suggests that PA is key to the cascade of growth signals that process following workouts and without it repair and growth potential is retarded. We theorize that increasing the concentration of PA via oral administration would amplify this growth signaling cascade.

Another interesting note is that PA binds to and activates p70S6K, even in the absence of mTOR (Nicholas Lehman et al, 2007). This suggests that PA can have anabolic potential at other times of day regardless of whether one has just exercised or not.

PA-induced activation of mTOR is also independent of a protein called wortmannin, an enzyme that inhibits mTOR activation by nutrients and growth factors. Therefore, while amino acids such as leucine can cause anabolism via mTOR activation, they can be inhibited by wortmannin. PA does not suffer this fate (see FIG. 2).

Prophetic doses of PA would be on the order of 1-4 grams per day, more preferably 1-1.5 grams per day. We theorize that such a dosing range would be viable based on similar dosing levels of leucine (which works through mTOR) and phosphatidylserine dosing. We expect that the dosing ought to be split into at least two doses per day, with at least one dose following an exercise session before the anabolic window closes (e.g., within 1-2 hours) to help amplify the effects of the workout and the effect of the post workout meal. Because PA works independently of the pathway that leucine works, we expect it will be advantageous to ingest the PA supplement with food, as it will complement the action of leucine or similar amino acids. If the user exercises at night, then it is probably best to ingest the PA supplement upon awakening, with food, and then again in the anabolic window following an exercise session. As an example, we expect that the post-exercise meal should include 20 to 100 grams of protein and/or an amino acid formula during the anabolic window. Depending on the source of the PA, e.g., lecithin, it would help with the taste and texture of the PA supplement (e.g., in drink mix form). Preferably, the concomitant protein is a complete protein containing all the essential amino acids. In addition or in the alternative, the protein is whey or partially hydrolyzed collagen protein, which would be extremely convenient in the form of a protein shake as well as taking it supplementally with a solid food source.

The PA to be included in the inventive composition may be prepared from soybeans, peanuts, wheat, oats, safflower, fish, milk, bovine liver, eggs, egg yolks, and other known sources of amino acids. The inventive composition may include nutritional supplements, such as protein, amino acids, .alpha.-lipoic acids, .beta.-hydroxy-.beta.-methyl butyrate, glycine propyline-L-carnitine, carnitine, Russian tarragon, gymnema sylvestre, bitter melon, cissus quadruangularis, cinnamon and fenugreek, leucine peptide, leucine, isoleucine, valine, anacyclus pyrethrum extract, nettle root extract, CLA, tribulus, mulberry, ribose, caffeine, beta alanine, ZMA, betaine, L-aspartic acid, carnosine, and the like.

We expect that, as a supplement for typical healthy people seeking improved muscle mass and strength, the inventive PA supplement is preferably taken orally, either as a pill, capsule, powder, or liquid drink type mix. In a hospital or medical setting for people with wasting diseases or who are bedridden for long periods of time, we expect that intravenous and/or other administration methods would be applicable as well.

Phosphatidylcreatine is a prophetic composition based on the union of the known ergogenic aid creatine and our prophetic anabolic aid phosphatidic acid (PA). Creatine is used to boost intracellular ATP stores within muscle tissue, thereby increasing performance potential. There already exists a wealth of information regarding the benefit of oral phophatidylserine (PS) for performance and cortisol control, and oral phophatidylcholine (PC) for performance and cognitive enhancement. We expect phosphatidylcreatine to enable significant increases in muscle mass and strength in mammalian users. One possible method of formulating phosphatidylcreatine is in a slurry type mix similar to that described in U.S. Pat. No. 6,399,661 to Golini concerning the manufacture of an oral creatine supplement. The creatine and phosphatidic acid are expected to be provided in the ratio of about 5 to 3. Phosphatidylleucine is another prophetic composition based on a union of PA and leucine which we expect to also prove to be an excellent anabolic aid. One possible method of formulating phosphatidylleucine is in a slurry type mix similar to that described above for phosphatidylcreatine. The leucine and phosphatidic acid are expected to be provided in the ratio of about 5 to 3. The prophetic anticipated amount of leucine to be provided is approximately 2-5 grams, more preferably about 3 grams. Optionally, the method includes the administration of leucine, isoleucine, and valine in a 2:1:1 ratio, e.g., 4 grams leucine, 2 grams isoleucine, and 2 grams valine.

The invention is not limited to the above description. For example, although it is preferred that PA be administered/ingested within the anabolic window following exercise, the inventive method also contemplates administering PA at other times of the day not tied to an exercise session. Similarly, while the preferred dosing is at least 1.0-1.5 grams/day of PA, it is expected that more PA may be consumed daily without adverse effects. Additionally, while the inventive method and composition are chiefly targeted for human consumption, it is contemplated to be used for/by any other mammals, e.g., horses, dogs, and the like. Dosing would likely be scalable by relative body weight of the mammal in question, e.g., horses may require is 10 to 40 grams, dogs may require 0.1 to 3 grams, etc.

Having described certain embodiments of the invention, it should be understood that the invention is not limited to the above description or the attached exemplary drawings. Rather, the scope of the invention is defined by the claims appearing hereinbelow and includes any equivalents thereof as would be appreciated by one of ordinary skill in the art.

What is claimed is:

1. A method of increasing muscle mass and strength in mammals, the method comprising the step of orally administering a composition comprising a therapeutically effective amount of approximately 0.5-4.0 grams of phosphatidic acid, wherein muscle mass and strength are increased, said composition further comprising a therapeutically effective amount of leucine, said composition including phosphatidylleucine.

2. A method of increasing skeletal muscle mass and strength in mammals, the method comprising the step of orally administering a composition comprising a therapeutically effective amount of phosphatidic acid to an exercising subject, wherein skeletal muscle mass and strength are increased, said composition further comprising a therapeutically effective amount of leucine, said composition including phosphatidylleucine.

3. A method of increasing skeletal muscle mass and strength in mammals according to claim 2, wherein the therapeutically effective amount of phosphatidic acid is approximately 0.5-4.0 grams per day.

4. A method of increasing skeletal muscle mass and strength in mammals according to claim 2, wherein the therapeutically effective amount of phosphatidic acid is approximately 1.0-1.5 grams per day.

5. A method of increasing skeletal muscle mass and strength in mammals according to claim 2, said oral administration step further comprising the step of dividing the therapeutically effective amount of phosphatidic acid into a plurality of doses per day with at least one dose being administered to the exercising subject within 1-2 hours following an exercise session.

6. A method of increasing skeletal muscle mass and strength in mammals according to claim 2, wherein said oral administration step is executed to the exercising subject following exercise during the anabolic window.

7. A method of increasing skeletal muscle mass and strength in mammals according to claim 6, further comprising the step of orally administering 20-100 grams of protein during the anabolic window.

8. A method of increasing skeletal muscle mass and strength in mammals according to claim 7, wherein the protein is a complete protein containing all the essential amino acids.

9. A method of increasing muscle mass and strength in mammals according to claim 7, wherein the protein is whey or partially hydrolyzed collagen protein.

10. A method of increasing muscle mass and strength in mammals according to claim 2, said composition further comprising a therapeutically effective amount of creatine.

11. A method of increasing muscle mass and strength in mammals according to claim 10, wherein said therapeutically effective amount of creatine is 3-20 grams.

12. A method of increasing muscle mass and strength in mammals according to claim 10, said composition including phosphatidylcreatine.

13. A method of increasing muscle mass and strength in mammals according to claim 1, wherein the therapeutically effective amount of phosphatidic acid is approximately 1.0-1.5 grams per day.

14. A method of increasing muscle mass and strength in mammals according to claim 1, said oral administration step further comprising the step of dividing the therapeutically effective amount of phosphatidic acid into a plurality of doses per day with at least one dose being administered within 1-2 hours following an exercise session.

15. A method of increasing muscle mass and strength in mammals according to claim 1, wherein said oral administration step is executed to an exercising subject following exercise during the anabolic window.

16. A method of increasing muscle mass and strength in mammals according to claim 15, further comprising the step of orally administering 20-100 grams of protein during the anabolic window.

17. A method of increasing muscle mass and strength in mammals according to claim 16, wherein the protein is a complete protein containing all the essential amino acids.

18. A method of increasing muscle mass and strength in mammals according to claim 16, wherein the protein is whey or partially hydrolyzed collagen protein.

19. A method of increasing muscle mass and strength in mammals according to claim 1, said composition further comprising a therapeutically effective amount of creatine.

20. A method of increasing muscle mass and strength in mammals according to claim 19, wherein said therapeutically effective amount of creatine is 3-20 grams.

21. A method of increasing muscle mass and strength in mammals according to claim 19, said composition including phosphatidylcreatine.

22. A method of increasing muscle mass and strength in mammals according to claim 1, wherein said therapeutically effective amount of leucine is 2-5 grams.

\* \* \* \* \*